United States Patent
Rucinski

(10) Patent No.: US 10,016,375 B2
(45) Date of Patent: Jul. 10, 2018

(54) MATERIALS AND METHODS FOR CONTROLLING INFECTIONS

(71) Applicant: Paul J. Rucinski, Ocklawaha, FL (US)

(72) Inventor: Paul J. Rucinski, Ocklawaha, FL (US)

( * ) Notice: Subject to any disclaimer, the term of this patent is extended or adjusted under 35 U.S.C. 154(b) by 0 days.

(21) Appl. No.: 15/050,239

(22) Filed: Feb. 22, 2016

(65) Prior Publication Data

US 2016/0235692 A1   Aug. 18, 2016

Related U.S. Application Data

(63) Continuation-in-part of application No. 14/568,925, filed on Dec. 12, 2014, now Pat. No. 9,642,820.

(60) Provisional application No. 61/915,281, filed on Dec. 12, 2013.

(51) Int. Cl.
| | | |
|---|---|---|
| *A61K 31/15* | (2006.01) | |
| *A61K 31/155* | (2006.01) | |
| *A61K 9/00* | (2006.01) | |
| *A61K 45/06* | (2006.01) | |
| *A61K 38/38* | (2006.01) | |
| *A61F 13/00* | (2006.01) | |

(52) U.S. Cl.
CPC ...... *A61K 31/155* (2013.01); *A61F 13/00063* (2013.01); *A61K 9/0048* (2013.01); *A61K 38/38* (2013.01); *A61K 45/06* (2013.01)

(58) Field of Classification Search
None
See application file for complete search history.

(56) References Cited

U.S. PATENT DOCUMENTS

| | | | |
|---|---|---|---|
| 2,090,354 | A | 8/1937 | Massman |
| 4,925,668 | A | 5/1990 | Khan et al. |
| 5,033,961 | A | 7/1991 | Kandler et al. |
| 5,725,311 | A | 3/1998 | Ponsi et al. |
| 5,906,278 | A | 5/1999 | Ponsi et al. |
| 5,908,865 | A * | 6/1999 | Doi ............ A61K 9/0014 514/635 |
| 5,944,713 | A | 8/1999 | Schuman |
| 5,956,794 | A | 9/1999 | Skiba et al. |
| 6,029,809 | A | 2/2000 | Skiba et al. |
| 6,558,686 | B1 | 5/2003 | Darouiche |
| 8,221,365 | B2 | 7/2012 | Keaty, Jr. et al. |
| 9,327,095 | B2 | 5/2016 | Ma |
| 9,642,820 | B2 | 5/2017 | Twomey et al. |
| 9,668,989 | B2 | 6/2017 | Twomey et al. |
| 2005/0013805 | A1 | 1/2005 | Tavori |
| 2010/0029779 | A1 | 2/2010 | Street et al. |
| 2011/0097372 | A1 | 4/2011 | Rucinski |
| 2011/0117223 | A1 | 5/2011 | Worthington et al. |
| 2011/0288363 | A1 | 11/2011 | Morgan et al. |
| 2011/0288507 | A1 | 11/2011 | Rucinski |
| 2012/0150131 | A1 | 6/2012 | Do et al. |
| 2013/0184230 | A1 | 7/2013 | Hu et al. |
| 2016/0279080 | A1 | 9/2016 | Twomey et al. |

FOREIGN PATENT DOCUMENTS

| | | |
|---|---|---|
| WO | 2008060380 A2 | 5/2008 |
| WO | 2011056486 A2 | 5/2011 |

OTHER PUBLICATIONS

Naphazoline product information (accessed at Drugs.com on Apr. 19, 2017).*
"*Staphylococcus aureus* in the Community—Information for Clinicians," NSW Government Health, accessed on May 11, 2016, from http://www.health.nsw.gov.au/Infections/factsheets/Pages/staphylococcus-aureus-community.aspx, pp. 1-5.
Bennett, Garrett. "How do I treat my sinus infection?" Natural & Home Remedies for Sinus Infections, New York Sinus Surgery, Nov. 1, 2013, pp. 1-6.
Cankaya, Hakan et al., "Effects of topical chlorhexidine applied to the rabbit nasal mucosa," Auris, Nasus, Larynx, 2003, 30:65-69.
Heard, Stephen O. et al., "Influence of Triple-Lumen Central Venous Catheters Coated With Chlorhexidine and Silver Sulfadiazine on the Incidence of Catheter-Related Bacteremia," Arch Intern Med., 1998, 158:81-87.
Johner, AR, et al., "Accidental Intra-Arterial Injection of Alcoholic Chlorhexidine-Complications and their Management." J. Clini Toxicol, 2012, 2(7): 1-2.
Orito, Kensuke, et al., "Effects of Single Intratracheal Exposure to Chlorhexidine Gluconate on the Rat Lung." Drug and Chemical Toxicology, 2006, 1 1-9.
Ruschulte, Heiner et al., "Prevention of central venous catheter related infections with chlorhexidine gluconate impregnated wound dressings: a randomized controlled trial," Ann Hematol., Jul. 2008, p. 1-6.
Schuerer, Douglas J.E. et al., "Effect of Chlorhexidine/Silver Sulfadiazine-Impregnated Central Venous Catheters in an Intensive Care Unit with a Low Blood Stream Infection Rate after Implementation of an Educational Program: A Before-After Trial*," Surgical Infections, 2007, 8(4):445-454.

* cited by examiner

*Primary Examiner* — Robert A Wax
*Assistant Examiner* — Melissa S Mercier
(74) *Attorney, Agent, or Firm* — Saliwanchik, Lloyd & Eisenschenk

(57) ABSTRACT

The subject invention provides materials and methods for reducing ocular infections in subjects. The materials and methods utilize chlorhexidine, which has been found to be unexpectedly non-toxic to humans and other animals in low concentrations. The lack of toxicity facilitates the use of chlorhexidine in contexts that were not previously thought possible.

5 Claims, No Drawings

MATERIALS AND METHODS FOR CONTROLLING INFECTIONS

CROSS-REFERENCE TO RELATED APPLICATIONS

This application is a continuation-in-part application of and claims the benefit of priority of U.S. patent application Ser. No. 14/568,925, entitled "Materials and Methods for Controlling Infections," filed Dec. 12, 2014, which claims the benefit of priority of U.S. Provisional Application Ser. No. 61/915,281, filed Dec. 12, 2013, the entire contents of all of which are hereby incorporated by reference as if fully set forth herein, under 35 U.S.C. § 119(e).

BACKGROUND OF THE INVENTION

The management and treatment of an infection-prone wound, a surgical site, a surgical incision, or otherwise infection-prone tissues in the body, has three primary objectives: (1) prevention of infection, (2) preservation and/or restoration of function, and (3) preservation and/or restoration of cosmetic appearance. The most important of these objectives is the prevention of infection. Success in the prevention of infection directly affects the healing process and the degree to which function and cosmetic appearance can be preserved and/or restored.

The number and virulence of bacteria present at a site are critical determinants of whether the site becomes infected. Experimental evidence suggests that a critical level of bacteria is approximately $10^5$ organisms per gram of tissue. Below this level, a site or a tissue typically heals; at levels greater than $10^5$ bacteria per gram of tissue, infections often develop. Dirty wounds, or wounds that have not been treated within six hours, are likely to be contaminated with bacteria at levels that are higher than the critical level. Reducing the number of bacteria in and around the wound is critical for avoiding infection and expediting wound healing.

Many of the viruses, bacteria, parasites, and fungi that can invade the human body and its tissues are also capable of attacking the surface or interior of the eye. The eye is a complex organ of many parts. Infectious eye diseases can be categorized in two ways. First, physicians normally address the part of the eye that is infected or inflamed. Conjunctivitis, for example, is an inflammation of the conjunctiva, the membrane of the inner eyelid and the inner corner of the eye's surface. Other possible locations of infection and inflammation include the eyelid (blepharitis), the eyelash (stye), the cornea (keratitis), the oil gland of the eyelid (chalazion), the lacrimal sac at the inner corner of the eye (dacryocystitis), the liquid inside the eye (vitritis), the retina and the blood vessels that feed it (chorioretinitis), or the optic nerve (neuroretinitis). Second, eye infections are also classified according to what is causing them.

Ocular histoplasmosis syndrome (OHS), for example, is caused by a fungus (the condition is also called chorioretinitis). It generally attacks the blood supply of the retina, on the inner rear surface of the eye. Fungal eye infections are extremely rare, but they can be very serious. The most common way for someone to develop a fungal eye infection is as a result of an eye injury, particularly if the injury was caused by plant material such as a stick or a thorn. All types of fungal eye infections must be treated with prescription antifungal medication, usually for several weeks to months. Natamycin is a topical antifungal medication that works well for fungal infections involving the outer layer of the eye, particularly those caused by fungi such as *Aspergillus Candida*, and *Fusarium*. Endophthalmitis is an infection of the inside of the eye (the vitreous and/or aqueous humor). There are two types of endophthalmitis: exogenous and endogenous. Exogenous fungal endophthalmitis occurs after fungal spores enter the eye from an external source. Endogenous endophthalmitis occurs when a bloodstream infection (for example, candidemia) spreads to one or both eyes.

Parasites such as *Acanthamoeba* which are a microscopic, free-living ameba (single-celled living organism) commonly found in the environment can cause rare, but severe, illness. *Acanthamoeba* causes three main types of illness involving the eye (*Acanthamoeba keratitis*), the brain and spinal cord (Granulomatous Encephalitis), and infections that can spread throughout the entire body (disseminated infection). *Acanthamoeba* is found worldwide. Most commonly, *Acanthamoeba* is found in soil, dust, fresh water sources (such as lakes, rivers, and hot springs), in brackish water (such as a marsh), and sea water. *Acanthamoeba* can also be found in swimming pools, hot tubs, drinking water systems (for example, slime layers in pipes and taps), as well as in heating, ventilating, and air conditioning (HVAC) systems and humidifiers. *Acanthamoeba keratitis* infection has been linked to contact lens use, although people who do not use contact lenses can also become infected. Poor contact lens hygiene or wearing contact lenses during swimming, hot tub use, or showering may increase the risk of *Acanthamoeba* entering the eye and causing a serious infection. However, contact lens wearers who practice proper lens care can also develop infection.

The most common eye infection is conjunctivitis caused by an adenovirus, picornavirus, e.g., enterovirus 70 and coxsackievirus A24, rubella virus, rubeola virus, herpes virues, varicella-zoster virus, Epstein-Barr virus, and bacteria such as gonorrhea or *chlamydia*. This type of infectious conjunctivitis is sometimes called pinkeye and is most common in children. Viral conjunctivitis is contagious because the virus can be spread from the eye to hands that then touch doorknobs and other surfaces that other people use. Hands can become contaminated by coming in contact with infectious tears, eye discharge, fecal matter, or respiratory discharges. There are other causes of infectious conjunctivitis, such as bacteria like *Staphylococcus aureus*. Bacterial infections occur most commonly in children and tend to result in longer-lasting cases of pinkeye. The most common types of bacteria that cause bacterial conjunctivitis include *Staphylococcus aureus, Haemophilus influenzae, Streptococcus pneumoniae, Moraxella catarrhalis*, and *Pseudomonas aeruginosa*. Bacterial conjunctivitis is highly contagious and is spread through direct hand-to-eye contact from contaminated hands and usually produces a thick eye discharge or pus and can affect one or both eyes. Globally, the bacterium *Chlamydia trachomatis* is the leading cause of preventable blindness of infectious origin. Trachoma is a chronic follicular conjunctivitis, which is transmitted from person-to-person, through shared items or by flies.

Methicillin-resistant *Staphylococcus aureus* (MRSA) infection is caused by *Staphylococcus aureus* bacteria—often called "staph." Decades ago, strains of staph emerged in hospitals that were resistant to the broad-spectrum antibiotics commonly used to treat them. These antibiotics include methicillin and other more common antibiotics such as oxacillin, penicillin, and amoxicillin. Dubbed MRSA, it was one of the first germs to be resistant to all but the most powerful drugs.

Staph bacteria are generally harmless unless they enter the body through a cut or other wound. In older adults and people who are ill or have weakened immune systems, ordinary staph infections can cause serious illness. Staph infections, including MRSA, occur most frequently among persons in hospitals and healthcare facilities, such as nursing homes and dialysis centers, who have weakened immune systems; however, in the 1990s, a type of MRSA began appearing in the wider community. Today, that form of staph, known as community-associated MRSA, or CA-MRSA, and is responsible for many serious skin and soft tissue infections and for a serious form of pneumonia. If not treated properly, MRSA infection can be fatal.

Eye infections caused by MRSA are on the rise. MRSA infections are spreading rapidly in the United States and worldwide. According to the Center for Disease Control and Prevention (CDC), the proportion of infections that are antimicrobial resistant has been growing. In 1974, MRSA infections accounted for two percent of the total number of staph infections; in 1995 it was 22%; and in 2004 it was nearly 63%. Additionally, recent research has suggested that 30-50% of the population carries MRSA colonies on their bodies all the time, helping to facilitate the spread of infection.

Vancomycin is one of the few antibiotics still effective against hospital strains of MRSA infection, although the drug is no longer effective in every case. Several drugs continue to work against MRSA, but MRSA is a rapidly evolving bacterium, and it may be a matter of time before it, too, becomes resistant to most antibiotics. New treatments for infection are needed.

Chlorhexidine is a chemical antiseptic, and it combats both gram positive and gram negative microbes. It is bacteriostatic, hampering the growth of bacteria, and bacteriocidal, killing bacteria. It is often used as an active ingredient in mouthwash designed to kill dental plaque and other oral bacteria. Chlorhexidine also has non-dental applications. For example, it is used for general skin cleansing, as a surgical scrub, and as a pre-operative skin preparation. Chlorhexidine is typically used in the form of acetate, gluconate, or hydrochloride, either alone or in combination with other antiseptics such as cetrimide. The use of chlorhexidine has been found to be surprisingly non-toxic in topical treatment of the eye. This lack of toxicity facilitates the use of chlorhexidine in contexts that were not previously thought possible. The present invention is based on new unexpected findings that demonstrate the ability of the provided compound to significantly reduce ophthalmic inflammation and infection.

See, for example, U.S. Published Application No. 2011-0288507A and U.S. Published Application No. 2011-0097372A, both of which are incorporated herein, by reference, in their entireties.

SUMMARY OF THE INVENTION

The current invention provides materials and methods for preventing or treating a subject at risk of or having inflammation or infection at an ocular site by administering a chlorhexidine formulation comprising the active agent chlorhexidine (herein referred to as chlorhexidine formulation), either directly or indirectly, to the site of the infection, or potential infection. In preferred embodiments, the chlorhexidine formulation is sterile.

Advantageously, it has been found that a chlorhexidine formulation can be administered to a subject according to the current invention without causing irritation or damage. Furthermore, when administered according to the procedures of the subject invention, the chlorhexidine formulation of the subject invention does not result in deleterious absorption of chlorhexidine, systemic toxicity, or fibrosis.

Based on these findings it is now possible to utilize a chlorhexidine formulation in novel and advantageous ways, as described herein, to effectively treat and/or prevent infections in the eye of a subject, e.g., infection or inflammation of the conjunctiva, styes, chalazion, dacryocystitis, blepharitis, keratitis, vitritis, chorioretinitis, and neuroretinitis.

Advantageously, the chlorhexidine formulations are useful against drug resistant microbes, including MRSA. Furthermore, microbes do not readily acquire resistance to the treatments of the subject invention.

In a preferred embodiment, the active agent is chlorhexidine gluconate, preferably at a concentration of about 1.0% or less, more preferably at about 0.1% or less, and even more preferably at about 0.05% or less, and for some uses at 0.02% or less. Chlorhexidine dissolved in plain water or in a salt-containing solution, saline for example, can be used according to the current invention.

In certain embodiments, the administration of the chlorhexidine formulation is followed by a rinse with, for example, saline. In other embodiments, no such rinse is applied. The aqueous solution, or other material, containing chlorhexidine may have other components including, for example, pH modifiers, buffers, local anesthetic agents, agents that promote healing (such as agents that help degrade biofilm), anti-microbial agents that stop infection, and other therapeutic and non-therapeutic components. In one embodiment, the chlorhexidine formulation "consists essentially" of an aqueous solution of chlorhexidine, which means that the solution contains no other active agent that materially, changes the ability of the solution to control microbial growth.

The chlorhexidine formulation as described herein can be used in a variety of applications directed at preventing and/or treating ocular inflammation or infection. Treatment can be applied for a subject at risk of or having infection or inflammation of the conjunctiva, styes, chalazion, dacryocystitis, blepharitis, keratitis, vitritis, chorioretinitis, and neuroretinitis.

The current invention also provides kits comprising the chlorhexidine formulation and devices for ocular administration of the chlorhexidine formulation to the subject. In preferred embodiments the chlorhexidine composition, the kits and the trays are sterile.

DETAILED DESCRIPTION

Methods of Treatment

Methods of treating a subject's (e.g., a human or animal) at risk of or having inflammation or infection of the eye are provided. Such methods comprise administering a chlorhexidine formulation, to a human or animal eye to provide at least one benefit to the eye.

The current invention provides materials and methods for preventing and/or reducing a subject at risk of the development of an infection or treating an existing infection at an site in a subject, i.e., conjunctivitis, chalazion, dacryocystitis, blepharitis, keratitis, vitritis, choriorretinitis, and neuroretinitis of the eye. The subject may be, for example, a human or other animal.

Chlorhexidine formulations can be administered to a subject according to the current invention without causing hemolysis or other deleterious effects on the blood, blood cells, or blood vessels of the eye. Furthermore, when administered according to the procedures of the subject invention, the chlorhexidine formulations of the subject invention do not result in deleterious absorption of chlorhexidine, systemic toxicity, or fibrosis.

Based on these findings it is now possible to utilize chlorhexidine formulations in novel and advantageous ways, as described herein, to effectively treat and/or prevent infections of or in the eye of a subject.

Advantageously, the chlorhexidine formulations of the subject invention are useful against drug resistant microbes, including MRSA. Furthermore, microbes do not acquire resistance to the treatments of the subject invention.

In one embodiment, the method of the subject invention comprises the steps of: (a) providing a sterile disinfectant chlorhexidine formulation comprising an active agent comprising chlorhexidine at a concentration of about 1% or less, and (b) administering the sterile disinfectant composition, directly or indirectly, to the ocular site of the subject at risk of or having inflammation or infection at the ocular site.

The site to which the chlorhexidine is applied can be any site in the eye that is at a risk of developing an infection or has an existing infection. Non-limiting examples of sites that are appropriate for the practice of the method of the current invention include the membrane of the inner eyelid and the inner corner of the eye's surface, or conjunctiva, the eyelid, the eyelash, the tear ducts, the cornea, the liquid inside the eye, the retina and the blood vessels that feed it and the optic nerve, pre-operative and post-operative surgical sites, and surgical incisions in the eye.

Advantageously, the chlorhexidine formulation of the subject invention is effective in preventing and combating infection, even when organic materials (including blood, tissue, and/or dirt and debris) are present.

The chlorhexidine formulation of the current invention contains an active agent that preferably comprises chlorhexidine at a concentration of less than about 1%, less than about 0.1%, less than about 0.05%, less than about 0.025%, or less than about 0.02%. The chlorhexidine can be, for example, chlorhexidine gluconate, chlorhexidine digluconate, chlorhexidine acetate, chlorhexidine diacetate, chlorhexidine hydrochloride, chlorhexidine dihydrochloride, or a combination thereof. The chlorhexidine may also be modified with, for example, a phosphate group to enhance efficacy, further reducing the likelihood of the development of resistant microbes. The chlorhexidine formulation can further contain one or more additional active agents. In certain embodiments, the chlorhexidine formulation contains no alcohol, or less than 1%, 5%, 10%, 25%, or 50% alcohol. In other embodiments, the chlorhexidine formulation is mixed with albumin or other protein-free agent known in the art (e.g., Ringer's solution, Normal Saline or sterile water for irrigation).

In specific embodiments, the chlorhexidine formulation can be used to reduce the formation of biofilm associated with conjunctivitis, or pink eye. In a further embodiment, the chlorhexidine formulation of the subject invention can be used to prevent or reduce eye infections.

In certain embodiments, the chlorhexidine formulation can be used for prophylactic treatment in new born subjects having infection as a result of including, but not limited to, *Chlamydia*, Gonorrhea, Syphilis, Group B *streptococcus*, *Candida*, other bacteria, Herpes Simplex virus, *Mycoplasma, Ureaplasma*, Bacterial vaginosis, Trychomonas, and pathogens known in the art as a result of contamination of the birth canal. Some microorganisms colonize the female external genital tract and during the delivery the fetus will contaminate by exposure to maternal blood and secretions in the birth canal. Specifically, Gram-positive and Gram-negative organisms, facultative anaerobes, aerobes, and yeasts.

Preoperative skin disinfection is the use of antiseptics at the surgical site prior to surgery to reduce the risk of infection. In certain embodiments, a subject may have a sensitivity or allergy to standard pre-operative disinfectants. Where it is indicated that the patient is allergic to shellfish, which may contain iodine, a non-iodine prep solution should be used. If the patient is allergic to iodine or strawberries, bananas, kiwis, or poinsettias, which contain elements of latex, chlorhexidine formulations are a appropriate alternative. In certain embodiments, preoperative showering and scrubbing with chlorhexidine is an effective regimen to reduce extrinsic intraoperative contamination of the surgical wound from skin bacteria.

Chlorhexidine gluconate is used as a skin cleanser for surgical scrubs, a cleanser for skin wounds, for preoperative skin preparation and germicidal hand rinses. The use of chlorhexidine gluconate in wound irrigation applications has been previously described. See, for example, U.S. Published Application No. 2011-0288507A and U.S. Published Application No. 2011-0097372A, both of which are incorporated herein, by reference, in their entireties. Those patent applications describe various uses of chlorhexidine gluconate-containing solutions. In certain embodiments, the materials and compositions of the current invention specifically exclude those uses that were described in U.S. Published Patent Application Nos. 2011-0288507A and 2011-0097372A.

The terms "about," "approximately," "approximate," and "around" are used in this patent application to describe some quantitative aspects of the invention, for example, the concentration of the active agent. It should be understood that absolute accuracy is not required with respect to those aspects for the invention to operate. When these terms are used to describe a quantitative aspect of the invention the relevant aspect may be varied by up to +/−10%. Thus, the terms "about," "approximately," "approximate," and "around" allow for variation of the various disclosed quantitative aspects of the invention by +/−1%, +−2%, +/−3%, +/−4%, +/−5%, +/−6%, +/−7%, +/−8%, +/−9%, or up to +/−10%. For example, a sterile disinfectant chlorhexidine formulation comprising about 1% active agent can contain 0.9% to 1.1% active agent.

Chlorhexidine Formulations

As used herein, the active agent chlorhexidine is a given chlorhexidine compound that refers to the compound itself, isomers and stereoisomers, if any, of the compound, suitable salts of the compound, derivatives of the compound and the like and mixtures thereof.

As use herein, the term "derivative" as it relates to a given chlorhexidine compound refers to a compound having a chemical make-up or structure sufficiently similar to the given compound so as to function in a manner substantially similar to a substantially identical to the given compound in the present compositions and/or methods.

Comfort and tolerability can be considered in formulating the present chlorhexidine formulations. The amount of organic compatible solute component employed in the present chlorhexidine formulations should be effective in providing at least one benefit to the eye of a patient without unduly adversely affecting the patient, for example, without unduly inducing discomfort, reflex tearing and the like adverse affects.

In one embodiment of the subject invention, the chlorhexidine formulation may be a low concentration solution of chlorhexidine that can be used to effectively prevent or treat infections. Advantageously, it has been found that these chlorhexidine formulations can be administered to a subject according to the current invention without causing deleterious effects. Furthermore, when administered according to the procedures of the subject invention, the chlorhexidine formulations do not result in deleterious absorption of chlorhexidine, system toxicity, or fibrosis.

Based on these findings it is now possible to utilize chlorhexidine formulations in novel and advantageous ways, as described herein, to effectively treat and/or prevent ocular infections in a subject.

In specific embodiments, the active agent chlorhexidine concentration is less than about 2%, less than about 1%, or less than about 0.1%. In a further embodiment, the chlorhexidine concentration is less than about 0.05%. In even further embodiments, the chlorhexidine concentration is between 0.02% and 0.05%. Specifically exemplified herein is the use of chlorhexidine gluconate.

In a specific embodiment, the active agent is chlorhexidine gluconate and is used according to the subject invention having the following chemical structure:

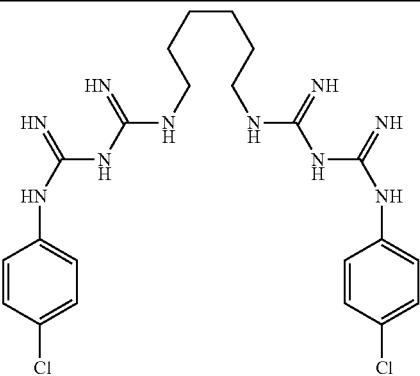

| CHG | |
|---|---|
| Systematic (IUPAC) Name | 1-[amino-[6-amino-[amino-(4-chlorophenyl)amino-methylidene]amino-methylidene]aminohexylimino]methyl]imino-N-(4-chlorophenyl)-methanediamine |
| Chemical Data | |
| Formula | $C_{22}H_{30}Cl_2N_{10}$ |
| Mol. weight | 505.446 g/mol |

The pH of the chlorhexidine formulation is preferably neutral or slightly acidic. Preferably the pH is 5.0 to 7.5. More preferably the pH is 5.5 to 7.0. These chlorhexidine solutions, particularly those intended for ophthalmic use, may be formulated as 0.01%-10% isotonic solutions, pH about 5-7, with appropriate salts.

In a preferred embodiment, the administration of the chlorhexidine formulation to an infection site in the eye results in a reduction in the number of bacteria or other microbes at the infection site when compared to either an untreated site or a site administered with saline or water that does not contain chlorhexidine. Advantageously, administration of the chlorhexidine formulation according to the subject invention can result in effective control of an infection without causing ocular damage.

Chlorhexidine is a cationic compound and the antibacterial activity of the drug is the result of attraction between positively charged chlorhexidine and negatively charged bacterial cell surfaces. Chlorhexidine becomes absorbed onto the cell surfaces of susceptible organisms, with specific and strong adsorption to certain phosphate-containing compounds. This disrupts the integrity of the cell membrane and increases permeability. [McEvoy, G. K. (ed.). American Hospital Formulary Service—Drug Information 2003. Bethesda, Md.: American Society of Health-System Pharmacists, Inc. 2003 (Plus Supplements)., p. 2620]PEER REVIEWED At low chlorhexidine concentrations, the drug usually exerts a bacteriostatic effect as the result of efflux of small molecular weight substances (eg, potassium, phosphorus). [McEvoy, G. K. (ed.). American Hospital Formulary Service—Drug Information 2003. Bethesda, Md.: American Society of Health-System Pharmacists, Inc. 2003 (Plus Supplements)., p. 2620]**PEER REVIEWED*

It has long been accepted in the medical community, that chlorhexidine cannot be used in the eye. There are a number of documented tragedies wherein use of chlorhexidine caused severe damage to the eye:

1) Chlorhexidine gluconate 4% may produce corneal damage (bullous keratopathy, epithelial defects, and corneal opacification) when applied to the eyes. [Ellenhorn, M. J., S. Schonwald, G. Ordog, J. Wasserberger. Ellenhorn's Medical Toxicology: Diagnosis and Treatment of Human Poisoning. 2nd ed. Baltimore, Md.: Williams and Wilkins, 1997., p. 1209]**PEER REVIEWED*

2) There have been reports of irreversible corneal damage in patients after after accidental eye exposure to chlorhexidine gluconate 4% solution in sustaining base (chlorhexidine gluconate 4% skin cleanser) being used for preoperative facial skin preparation. [McEvoy, G. K. (ed.). American Hospital Formulary Service—Drug Information 2003. Bethesda, Md.: American Society of Health-System Pharmacists, Inc. 2003 (Plus Supplements)., p. 2619]PEER REVIEWED

3) Eye decontamination. If eye exposure has occurred, the eyes should be vigorously irrigated and a careful ophthalmologic exam should be performed for corneal injury. If an injury has occurred, an ophthalmologic consultation should be obtained. [U.S. Environmental Protection Agency/Office of Prevention, Pesticides, and Toxic Substances. Reigart, J. R., Roberts, J. R. Recognition and Management of Pesticide Poisonings. 5th ed. 1999. EPA Document No. EPA 735-R-98-003, and available in electronic format at: http://www.epa.gov/pesticides/safety/healthcare p. 200]PEER REVIEWED

4) Chlorhexidine diacetate . . . is highly acutely toxic when applied to the eye. /Chlorhexidine diacetate/ [USEPA/Office of Pesticide Programs; Reregistration Eligibility Decision Facts—Chlorhexidine diacetate. EPA-738-F-96-25 Sep. 1996. Available from the Database Query page at http://cfpub.epa.gov/oppref/rereg/status.cfm?show=rereg as of Mar. 11, 2004.]PEER REVIEWED

5) /CASE REPORTS/ In three consecutive cataract operations, chlorhexidine was inadvertently used as an intraocular irrigating solution as a result of inattentiveness of an assistant. In two of the three patients, corneal endothelium damage was so severe that penetrating keratoplasty had to be performed. Further effects included pronounced iris atrophy, anterior chamber applanation, and a retrocorneal membrane. In one case, an increase in intraocular pressure developed. No effects were observed in the retina or optic nerve. Inadvertently using chlorhexidine for intraocular irrigation has far-reaching consequences for the affected eye and is recognizable by streak formation in the anterior chamber when intraocular infusion is initiated. [Anders N et al; J Cataract Refract Surg 23 (6): 959-62 (1997)]PEER REVIEWED

Despite the long-standing understanding in the art that chlorhexidine causes damage to the eye and is not appropriate for ocular administration, the unexpected discovery is disclosed herein that reducing the concentration of chlorhexidine to a certain level avoids problems with ocular administration while at the same time serves to treat infections and inflammation in the eye.

Examples of additional active agents that can be administered to a subject in accordance with the subject invention include, but are not limited to, anti-bacterial agents, anti-viral agents, fungicidal agents, chemotherapeutic agents, topical antiseptics, anesthetic agents, oxygenated fluids and/ or agents, antibiotics, diagnostic agents, homeopathic agents, agents that stop bleeding, and over-the-counter medications/agents. In one embodiment, the additional agent can be an anti-microbial peptide (AMP). AMPs are well known in the art.

In one broad aspect, chlorhexidine formulations are provided comprising a carrier component, advantageously an aqueous carrier component, and an effective amount of a tonicity component including a material selected from compatible solute components, for example, one or more of certain compatible solute agents, and mixtures thereof. In one very useful embodiment, the tonicity component comprises a material selected from erythritol components and mixtures thereof. In one additional embodiment, the tonicity component comprises a material selected from combinations of at least two different compatible solute agents.

Xylitol or erythritol used alone may require prolonged contact time to allow them to function effectively as a compatible solute component, for example, due to the time needed for cellular uptake. However once in situ, for example, within ocular surface cells, the beneficial action of balancing hypertonic conditions advantageously is longer than with an equivalent amount of glycerol, which moves more quickly into and out of cells. Such longer lasting benefit, and less frequent dosing, can be obtained without blurred vision.

In certain embodiments, the chlorhexidine formulation may be combined with albumin or other synthetic or natural protein(s) or amino acids suitable for ophthalmic administration. Examples of proteins that may be used in the formulations include, but are not limited to, silk protein, mucin, PRG4, lactoferrin, transferrin, caeruloplasmin and lacrimal gland peroxidase. In addition, the chlorhexidine formulation may be combined with a protein-free agent known in the art such as Sterile Water for Irrigation, Ringer's solution or other solution of several salts dissolved in water for the purpose of creating an isotonic solution relative to the bodily fluids of a subject. The Ringer's solution may be designed to substitute for the blood plasma, hemolymph, or other extracellular fluids of any species. Preferably, this combination of either albumin or a protein free agent, i.e., Ringer's solution, and the chlorhexidine formulation can be simultaneously applied as an endothelial surface bath or via separate bottles or with two nozzles, each dispensing a different agent. In an alternative embodiment, the chlorhexidine formulation may be used for the endothelial surface bath without albumin or other protein free agent.

In another broad aspect, chlorhexidine formulations are provided comprising a carrier, for example, an aqueous carrier, component, and an effective amount of a material selected from inositol components, xylitol components and mixtures thereof. The osmolality of such compositions are often higher or greater than isotonic, for example, in a range of at least 310 to about 600 or about 1000 mOsmols/kg.

In a further broad aspect, chlorhexidine formulations are provided which comprise a carrier, for example, an aqueous carrier, component, and an effective amount of a tonicity component comprising a material selected from carnitine components and mixtures thereof. In a particularly useful embodiment, the chlorhexidine formulation has a non-isotonic osmolality.

In an additional aspect, chlorhexidine formulations are provided which comprise a carrier, for example, an aqueous carrier, component, and an effective amount of a tonicity component comprising a material selected from a mixture or combination of compatible solute agents, for example, selected from mixtures of one or more polyol components and/or one or more amino acid components.

For the purpose of this invention, a plain aqueous solution of the active agent (i.e., chlorhexidine) comprises the active agent and/or a second agent in a solution of water that is essentially devoid of solutes that provide osmolarity to the solution, for example, a salt or a sugar. For the purpose of this invention, an isotonic solution refers to a solution having the same osmotic pressure as blood. Typically, isotonic solutions contain about 0.85% of NaCl in water. Accordingly, an isotonic solution containing the active agent according to the current invention refers to a solution of the active agent and/or a second agent in about 0.85% NaCl in water.

Topical formulations of chlorhexidine may be prepared as described for local and systemic administration. The resulting mixture may be a solution, suspension, emulsions or the like and are formulated as creams, gels, ointments, emulsions, solutions, elixirs, lotions, suspensions, tinctures, pastes, foams, aerosols, irrigations, sprays, suppositories, bandages, dermal patches or any other formulations suitable for topical administration.

For one of skill in the art, it is possible to make the chlorhexidine formulations as thick fluids and gels that are retained for greater periods on the ocular surface than thin fluids, with the trade-off often being a transient vision blur. Thick fluids and gels however have the advantage of less frequent dosing to deliver a given amount of active agent.

The chlorhexidine formulations may be formulated for local or topical application, such as for topical application to the mucous membranes, such as in the eye, in the form of gels, creams, and lotions and for application to the eye. Topical administration is contemplated for transdermal delivery and also for administration to the eyes or mucosa.

For example, if the chlorhexidine formulation is a solution, drops of it may be applied to the eye, e.g., from a conventional eye dropper. In general, the present chlorhexidine formulations may be applied to the surface of the eye in substantially the same way as conventional ophthalmic compositions are applied. Such administration of the present compositions does provide substantial and unexpected benefits, as described elsewhere herein.

Spectrum of Activity

Chlorhexidine is active against aerobic and anaerobic gram-positive and gram-negative bacteria. Chlorhexidine also has activity against *Chlamydia trachomatis*, certain fungi, and certain viruses.

Chlorhexidine is highly active against a variety of gram-positive aerobic bacteria, including *Streptococcus* mutants, *S. pyogenes* (group A β-hemolytic streptococci), *S. salivarius*, and *S. sanguis*. Chlorhexidine is active against *Staphylococcus aureus, S. epidermidis, S. haemolyticus, S. hominis*, and *S. simulans*. Chlorhexidine is active against both oxacillin-resistant (ORSA) and oxacillin-susceptible staphylococci (also known as methicillin-resistant [MRSA] or methicillin-susceptible staphylococci). Chlorhexidine is active against *Enterococcus*, including *E. faecalis* and *E. faecium*, and is active against both vancomycin-susceptible and vancomycin-resistant strains.

Chlorhexidine is also active against some anaerobic bacteria. Chlorhexidine is active against some strains of *Bacteroides, Propionibacterium, Clostridium difficile*, and *Selenomonas*, but is less active against *Veillonella*.

Chlorhexidine has activity against *Candida albicans, C. dubliniensis, C. glabrata* (formerly *Torulopsis glabrata*), *C. guillermondii, C. kefyr* (formerly *C. pseudotropicalis*), *C. krusei, C. lusitaniae*, and *C. tropicalis* (formerly *C. parapsilosis*). Chlorhexidine also has activity against dermatophytes, including *Epidermophyton floccosum, Microsporum gypseum, M. canis*, and *Trichophyton mentagrophytes*.

Chlorhexidine also has antiviral activity against viruses that have a lipid component in their outer coat or have an outer envelope such as cytomegalovirus (CMV), human immunodeficiency virus (HIV), herpes simplex virus types 1 (HSV-1) and 2 (HSV-2), influenza virus, parainfluenza virus, and variola virus (smallpox virus).

In addition to killing bacteria, the chlorhexidine formulations can also "depathogenize" certain bacteria including, for example, *Escherichia coli* and *Klebsiella aerogenes*, making these bacteria less potent to cause infection.

In a preferred embodiment, the administration of the chlorhexidine formulation to an infection site results in a reduction in the number of bacteria or other microbes at the site when compared to either an untreated site or a site administered with saline or water that does not contain chlorhexidine. Advantageously, and unexpectedly administration of the chlorhexidine formulation according to the subject invention can result in effective control of an infection without causing ocular damage.

Modes of Administration

Chlorhexidine formulations described herein can be administered using any of a wide range of currently-available delivery devices, systems, and methods. The methods of the subject invention can be used in conjunction with the delivery of a chlorhexidine formulation as in an eye wash, eye gel, and eye cream. The chlorhexidine formulations can also be formulated as a spray or mist to treat appropriate ocular sites.

In certain embodiments of the current invention, the chlorhexidine formulation is administered to a healing tissue site via a patch, bandage, or dressing containing the chlorhexidine; a thick viscous solution containing the chlorhexidine; or a suture containing chlorhexidine.

In a further embodiment of the invention, after administration of the chlorhexidine formulation to a site or a tissue, the site or the tissue is rinsed with, for example, a sterile solution free of the active agent. Examples of solutions free of the active agent include, but are not limited to, plain water, saline, and isotonic solutions free of the active agent. The rinsing can be performed by administering the solution free of the active agent to the site and removing the resultant solution from the site or the tissue by, for example, suction. In certain embodiments, the rinsing is performed within about 1 minute to about 10 minutes, about 2 minutes to about 5 minutes, or about 3 minutes from the time of administering the sterile disinfectant composition to the site in the subject. In other embodiments, suction is performed, with or without rinsing.

Under optimal circumstances, the methods of the subject invention are utilized by trained medical technicians; however, because of the simplicity and convenience of the subject invention, they can be used to greatly enhance the effectiveness of the administration of the disinfectant composition regardless of the training level of the operator performing the irrigation.

The subject can be a mammal. Non-limiting examples of mammals that can be treated according to the methods of the current invention include humans, non-human primates, dogs, cats, equines, bovines, and pigs.

Following are examples that illustrate procedures for practicing the invention. These examples should not be construed as limiting.

EXAMPLES

Example 1

Ocular Applications

In certain other embodiments of the current invention, the chlorhexidine formulation is administered to an ocular site for treatment of conjunctivitis, stye, blepharitis, keratitis, vitritis, chorioretinitis, or neuroretinitis, as an ophthalmic composition containing chlorhexidine. The ophthalmic composition can be, for example, a solution, suspension, or an ointment, a cream, a gel, containing the active agent chlorhexidine.

In a specific embodiment, a chlorhexidine formulation is applied to the eye in conjunction with an eye surgery procedure. The eye surgery procedure may be, for example, cataract surgery, retina surgery, lens replacement surgery, or surgery to correct traumatic damage including, but not limited to, corneal abrasion. The chlorhexidine formulation may be applied before, during, or after the surgery. The chlorhexidine formulation can also be used to treat pink eye.

The concentration of the chlorhexidine may be less than 4%, less than 1%, less than 0.16%, preferably less than 0.05%, less than 0.02%, or even less than 0.01%. The administration of the chlorhexidine formulation may be followed by a rinse with, for example, saline, but does not have to be followed by a rinse.

In one embodiment, the subject invention provides a container with a sterile chlorhexidine solution with an eye dropper contained therein, or associated therewith. The container may itself be sterile for use in a surgical setting.

Example 2

Kits

A further embodiment of the current invention provides kits comprising a sterile chlorhexidine formulation and devices for administration of the chlorhexidine formulation to the ocular site of the subject.

The devices for the administration of the chlorhexidine formulation to the site of the subject include, but are not limited to, a bottle for administering the plain aqueous solution of the active agent or the isotonic solution of the active agent to the site, a transdermal patch, a porous material, a sponge, or sutures. This can also be achieved via the port on minimally invasive surgery trocars and other such devices.

Non-limiting examples of the kits include, a plain aqueous solution of the active agent, an isotonic solution of the active agent, a plain aqueous solution of the active agent at a 2× concentration of the active agent compared to the final working solution and a solution free of active agent having 2×. isotonicity, the active agent in a solid form and sterile water or sterile isotonic solution, a transdermal patch containing the active agent, a porous material containing the active agent, a sponge containing the active agent, a thick viscous solution containing the active agent, a mist spray containing the active agent, sutures containing the active agent, an ophthalmic emulsion containing the active agent, an ophthalmic solution containing the active agent, an ophthalmic suspension containing the active agent, an ophthalmic ointment containing the active agent.

The kits including custom packs can be used to practice the methods of the current invention. For example, a user can use a kit comprising a plain aqueous solution of the active agent or the isotonic solution of the active agent by administering the solution of the active agent to the ocular site of the subject. Similarly, a user can mix equal amounts of the plain aqueous solution of the active agent at a 2× concentration and the solution free of active agent having 2× isotonicity to prepare a working isotonic solution of the active agent. A user can also dissolve the active agent in the solid form in sterile water or sterile isotonic solution to prepare a working isotonic solution of the active agent.

In another embodiment, provided is a kit that includes a first container containing a composition that comprises chlorhexidine at a concentration of 1% or less and a second container containing an aqueous solution containing ophthalmic-suitable protein or amino acid, or Ringer's solution. The containers may share a common nozzle, or each have their own nozzle for dispensing the formulation. In a specific embodiment, the container is squeezable and the nozzle produces drops that may be dropped into the eye of a subject.

It should be understood that the examples and embodiments described herein are for illustrative purposes only and that various modifications or changes in light thereof will be suggested to persons skilled in the art and are to be included within the spirit and purview of this application and the scope of the appended claims.

What is claimed is:

1. A method for treating a subject at risk of, or having, inflammation or infection at an ocular site, wherein said method comprises administering to the ocular site of the subject a formulation that consists of an aqueous solution of chlorhexidine at a concentration of from 0.02% to 0.1% and, optionally, one or more further ingredients selected from anti-bacterial agents, anti-viral agents, fungicidal agents, anesthetic agents, and buffers.

2. The method of claim 1, wherein the ocular site is an infected or inflamed condition selected from the group consisting of: conjunctivitis, stye, chalazion, dacryocystitis, blepharitis, keratitis, vitritis, chorioretinitis, and neuroretinitis.

3. The method of claim 1, wherein the concentration of chlorhexidine is about 0.05% or less.

4. The method of claim 1, wherein the chlorhexidine is chlorhexidine gluconate.

5. The method, according to claim 1, wherein the ocular site is infected.

* * * * *